United States Patent [19]

Terschüren et al.

[11] 4,131,027

[45] Dec. 26, 1978

[54] APPARATUS FOR ULTRASONIC INSPECTION OF THE WELDING SEAM OF LARGE PIPES

[75] Inventors: Wolfgang Terschüren; Karl Ries, both of Mülheim; Dieter Lather, Rheurdt, all of Fed. Rep. of Germany

[73] Assignee: Mannesmann Aktiengesellschaft, Dusseldorf, Fed. Rep. of Germany

[21] Appl. No.: 767,353

[22] Filed: Feb. 10, 1977

[30] Foreign Application Priority Data

Feb. 18, 1976 [DE] Fed. Rep. of Germany ....... 2607011

[51] Int. Cl.$^2$ .......................................... G01N 29/04
[52] U.S. Cl. .................................................. 73/638
[58] Field of Search .............. 73/67.5 R, 67.7, 67.8 R, 73/67.9, 71.5 US, 618, 622, 637, 638, 639, 640, 641

[56] References Cited

U.S. PATENT DOCUMENTS

| | | | |
|---|---|---|---|
| 3,213,676 | 10/1965 | Makous | 73/611 |
| 3,289,468 | 12/1966 | Van der Veer et al. | 73/637 |
| 3,350,925 | 11/1967 | Coy | 73/638 |
| 3,371,524 | 3/1968 | Wloszek | 73/639 |
| 3,472,064 | 10/1969 | Kortenhoven | 73/634 |
| 3,575,044 | 4/1971 | Gibbs et al. | 73/612 |
| 3,952,582 | 4/1976 | Graham et al. | 73/637 |

*Primary Examiner*—Stephen A. Kreitman
*Attorney, Agent, or Firm*—Smyth, Pavitt, Siegemund, Jones & Martella

[57] ABSTRACT

A pipe is reeled onto and over a stand having several positioning rollers to serve as reference for the pipe inspection devices. These devices include a plurality of transducers for longitudinal flaw detection arranged in pairs and along opposite sides of the seam, the transducers being in water tanks hung in gimbals on individual swing arms. Four additional transducers for transverse flaw detection are arranged in a tank hung also in gimbals for positioning the tanks so that it engages the seam while the transducers are aligned with the seam. A gimbal hung tank with two edge probing transducers engages lastly the pipe seam.

7 Claims, 11 Drawing Figures

APPARATUS FOR ULTRASONIC INSPECTION OF THE WELDING SEAM OF LARGE PIPES

BACKGROUND OF THE INVENTION

The present invention relates to equipment for inspecting the welding seam of submerged - arc-welded, large pipes, involving particularly the welding seam proper and the border or edge zones of the seam as interfacing with the pipe material, for detecting any flaws.

It has been suggested to place electro-mechanical transducers in particular relation to such a welding seam and to undertake, sequentially as to each seam increment, tests for locating longitudinal flaws, transverse flaws or edge flaws. Particularly, longitudinal flaws are detected through differently positioned transducers being laterally displaced from the welding seam by different distances therefrom, so as to maximize localization of the interaction of the ultrasonic energy with the welding seam and any defect therein. Transverse flaws are detected by means of ultrasonic transducers arranged along the seam, and edge zone flaws are detected by means of transducers arranged above the border between the seam and the pipe proper.

SUMMARY OF THE INVENTION

It is an object of the present invention to provide equipment which permits inspection of a welding seam as outlined above, and involving particularly sequential detection of longitudinal flaws, transverse flaws and flaws in the seam/pipe border zone. In particular, that equipment must meet the following requirements.

The seam must have a down or 6 o'clock position during testing and inspection. The transducers must be adjusted as to their test position in a reproducible manner, whereby the angle of incidence of the emitted ultrasonic bursts must be predeterminable and fixed in such a manner that that angle is indeed established when the transducers are moved into testing position. These angles must be establishable to have meaning independent from the geometry of the pipe and must be comparable for different test stands. These angles must be maintained throughout the test without automated or other kind of change during a test run.

In accordance with the preferred embodiment of the present invention, it is suggested to mount the transducers individually or in groups in containers for coupler fluid, e.g., water tanks, and these containers are mounted in gimbals. The gimbal mounts, in turn, are adjusted and positioned so that the containers assume a particular position in relation to the pipe to be tested which, in turn, positions the transducers.

In the preferred form of practicing the invention, the transducers for longitudinal flaw detection are mounted in pairs to opposite sides of the welding seam with individual adjustment towards and away from the seam, and each transducer is mounted in its own container. The transducers for the edge zone are preferably mounted in a common container being also hung in gimbals, and further being up and down adjustable. The transducers for the transverse flaw detection are also mounted in a common tank, and are individually adjustable in relation to each other in the container, while the container is hung in gimbals.

The transducers for longitudinal flaw detection have their individual, gimbal-suspended container further disposed on swing or pivot arms which are biased so that the containers engage the pipe. The pivot point for each arm is individually adjusted in the horizontal, that is to and from a vertical plane which runs through the center axis of the pipe and the center line of the weld. The gimbal mounted container for the transducers for detecting the transverse flaws, is pivoted up and down by a biased lever to fix the position of these transducers relative to the welding seam, as the transducers are aligned with the seam. The gimbal mounted container for the edge zone transducers is vertically positionable and biased for retaining an engaging position with the seam. The transducers in the container are preferably hung in gimbals individually and spring-biased for proper orientation alongside and to both sides of the seam.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
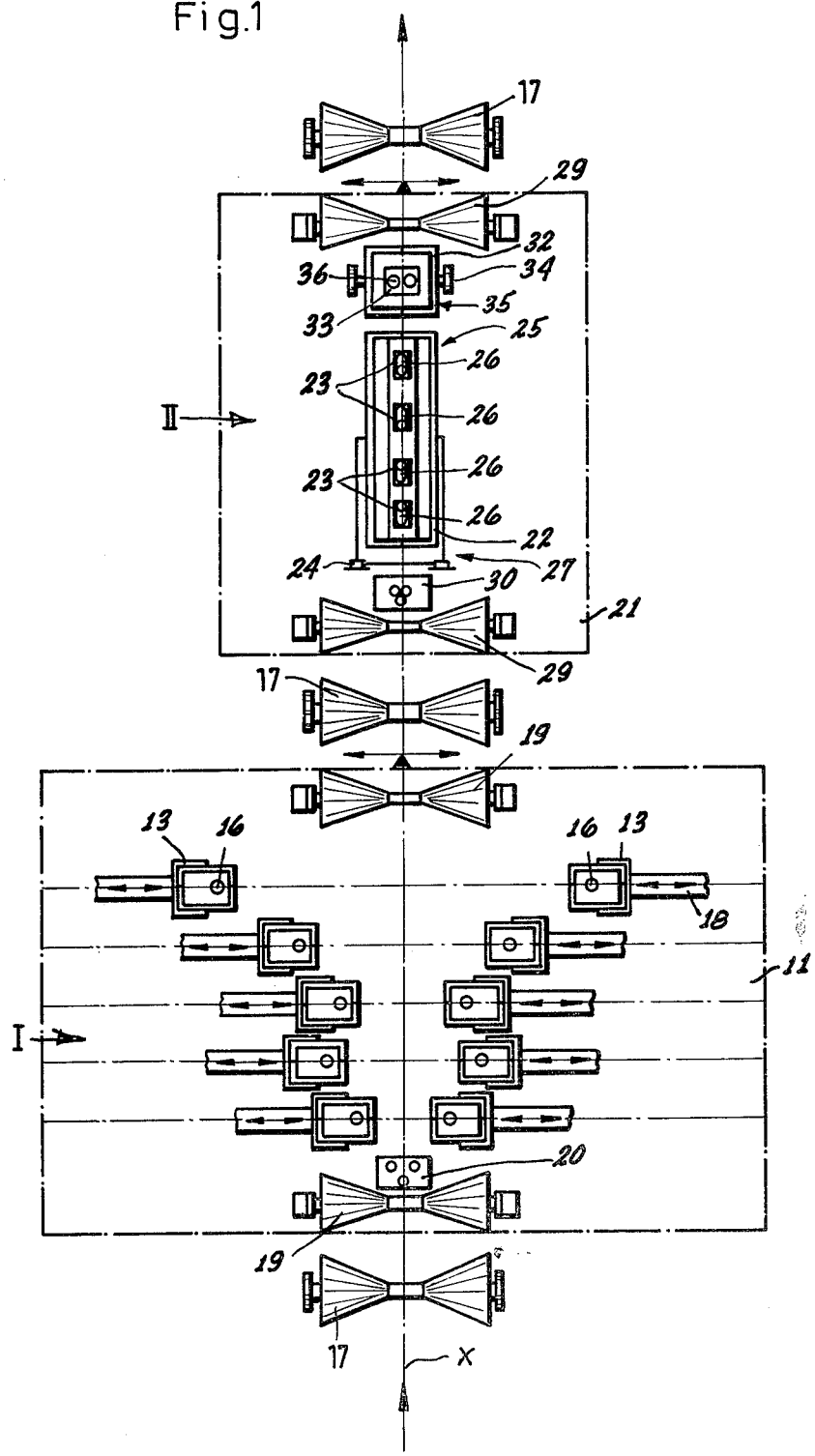
FIG. 1 is a top view of the testing equipment incorporating the preferred embodiment of the invention.

Proceeding now to the detailed description of the drawings, the figures show a pit 2 in a suitable foundation in which is suspended a carriage 1 having side arms, such as 3, which engage suitable tracks or roller beds 4 or the like. The double arrow denotes the direction of movement. In particular, the carriage 1 is to move at right angles to the axis of a pipe R to be tested.

A support 5 is held in the carriage 1 by means of several hydraulic drives 7 which may move the support up and down. A table or base plate 11 is mounted on support 5 for tilting about an axis 6 (see curved double arrow) which extends parallel to the axis of pipe R. The tilt or pivot motion is limited by stop elements 8.

A second support (not shown) is disposed behind the support 11 (as per the plane of the drawing of FIG. 2), and is driven and positioned vertically by a drive set similar to drive 7. Also, there is a table or base plate 21 (FIG. 1) pivotally mounted on that plate with pivots on an axis that is parallel to or even coincides with axis 6.

As is schematically shown in FIG. 1, a fixed set of track rollers 17 is mounted along a track path, and the rollers 17 illustrated in FIG. 1 are actually a portion of a roller track which continues at the top and at the bottom of the FIG. 1. The rollers 17 may be fixedly mounted.

The table 11 carries two pairs of prism rollers 19, one set being first in line for an incoming pipe R, and one being adjacent the particular roller 17 that is disposed between tables 11 and 21. Table 21 has analogously two pairs of prism rollers 29.

The table or base plate 11 carries a table 10 by means of support legs 12, the table being actually biparted to accommodate the pipe R in between. The table or tables 10 has a plurality of slots serving as bed and guiding means for slide elements 14. Each slide element can be manually adjusted towards and away from the pipe R. It is important that these bed-defining slots are accurately aligned in pairs and their position is, moreover, at exactly right angles to the tilt axis 6. For reasons below, these places then slides or carriages 4 in particular reproducable relation to the axis of a pipe R.

Arms and levers 18 extend from the slide elements 14 respectively; the levers are pivotally mounted. The pivot axes extend parallel to axis 6 in each instant; or, to say it differently, the pivot axes extend at right angles to the direction of movement of the slide 14 in its bed.

Each arm 18 is operated individually by a drive element 28 being mounted underneath table 10. The drives or drive elements 28 are basically hydraulic units for fast positioning. They are, however, constructed to switch over to pneumatic operation of its plunger engaging arm 18 so that a more resilient bias is provided thereafter.

A cardan or gimbal mount, such as 15, is provided at the end of each arm for cardanically mounting a water tank 13, being capable of pivoting about two horizontal axes accordingly. The water tank 13, in a more general sense, is a container for coupler fluid and each such container on an arm 18 contains also a transducer such as 16.

As can be seen from FIG. 1, plural such transducers 16 are disposed at variable distances from a center axis X of the system. This involves particularly the group I of altogether ten transducer 16, being individually mounted in gimbals and on the end of pivoting arms whose pivot axes are adjustable in the horizontal towards and away from a plane that runs vertically through axis X. This axis X is the track axis, and, in FIG. 1, it is the projection of the pipe's axis into the plane of the drawing. As far as table 11 is concerned, that axis X, in turn, is established by the prism rollers 19 which, by virtue of their position and construction hold, in turn, a pipe when in such a position that the axis of that pipe lies in a vertical plane that runs through the axis X. Therefore, the rollers 19 sense the position of a pipe on track rollers 17, and the transducers 16 are adjustably held in relation to that position of the table 11 and its attachments.

Considering any fixed adjustment positions of a slide 14 in its bed, pivotal adjustment of the arm 18 and of the gimbal mount for each transducer inscribes a (hypothetical) circle which has a definite and invariable position to that vertical plane as well as to any particular pipe on the positioning track as particularly defined by the rollers 19.

As to any particular pipe R, as far as its curvature is concerned, the combined adjustment of lateral position of the respective slide 14 and pivot position of the arm, defines a particular point of engagement with the pipe. As the gimbal mount permits full engagement of the respective container with the pipe's surface, the system is invariant as to the particular angle of incidence of the vibrations upon interaction of the respective transducer with the pipe's surface.

Aside from the elements as described thus far, plate or table 11 carries in addition a sensing device 20 which includes, e.g., a source of electromagnetic h-f signals and two pickup devices to monitor the interaction of the pipe with the h-f energy to determine the position of the welding seam. The device 20 operates a mechanism, known per se, which causes a pipe to rotate. That device is disposed upstream of the testing equipment which, in the case of FIG. 1, is below the bottom of that figure. Rotating a pipe is known per se and does not per se constitute a portion of the invention. It is, however, important that the input for such pipe rotation and control is particularly and fixedly disposed on table 11. Thus, the sensors define a null position for a pipe seam to be on that axis X, which is, of course, the 6 o'clock for any pipe on the track, and in particular engagement with the prism rollers 19.

The table 21 serves as support for the test group II. This test group includes particularly the four transducers 26. A particular stand (shown only in parts, 24) on table 21 pivots a short, one arm lever 27, having configuration of a pivoted frame and supporting a cardan or gimbal mount 25. Arm 27 pivots about a horizontal axis, i.e., an axis extending parallel to the plane of table 21. As a consequence, the cardan mount 25 can be moved up and down. A water tank 22 is cardanically mounted by mount 25. The arm 27 may be pivoted by means of a hydraulic drive (not shown, similar to 29), and held e.g., pneumatically in the adjusted position in which the water tank 22 will engage a pipe from below.

A plurality of transducer holders 23 are mounted in the tank 22, respectively, for the ultrasonic transducers 26. The holders 23 are individually adjustable, so that these transducers are adjustable with respect to each other inside of coupler fluid container 22. These transducers are aligned in and along an axis which registers with a second sensing device 30 for detecting the position of the welding seam. Specifically, the sensing device 30 is disposed with respect to an axis that runs parallel (in a vertical plane) to axis X and is specifically defined by the two sets or pairs of prism rollers 29. Upon vertically adjusting the table 21 that axis will, in fact, coincide with axis X or nearly so to offset any tolerances.

Figure 2:
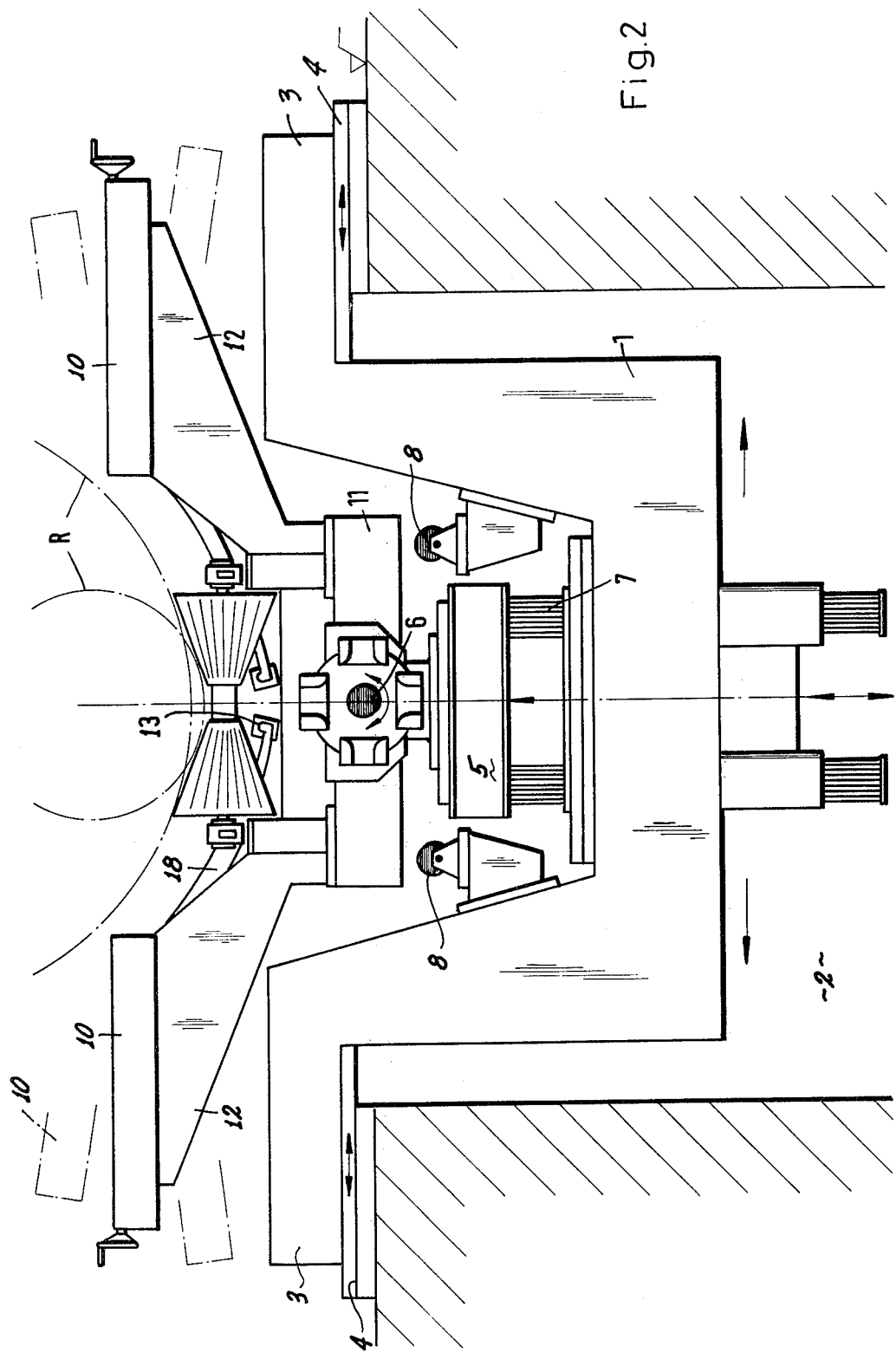
FIG. 2 is a side and section view of the equipment shown in FIG. 1.
Figure 3:
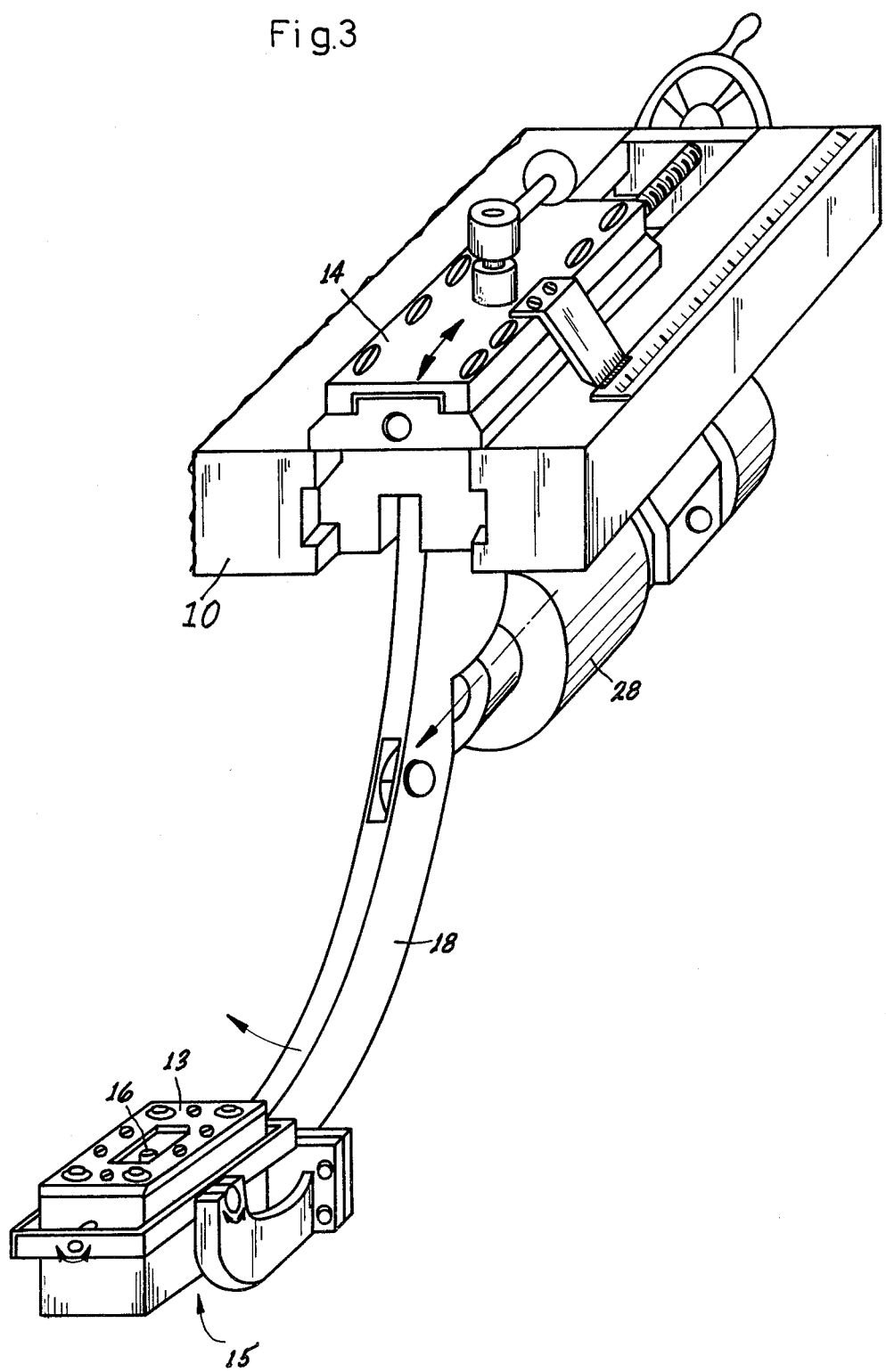
FIG. 3 is a perspective view of a transducer holder within the equipment shown in FIGS. 1 and 2, the transducer being particularly provided for detecting longitudinal flaws.

Another water tank 32 is cardanically mounted in a mount 35. Two holders 33 are individually cardanically suspended or gimbal-mounted in the tank or coupler fluid container 32. The holders 33 are provided for individually holding two transducers 36 in symmetric relation to the line as defined by the sensors or detectors 30 and by the transducers 26. The two gimbal mounted holders 33 for the two transducers are preferably individually spring-biased. The gimbal mount 35 for tank or container 32 is, in turn, mounted for vertical adjustment in a stand 34, so that the container 32 in its mount can be moved up and down, e.g., by a hydraulic drive (not shown). The equipment as well as conventional supplementary equipment operates as follows during a test sequence. Initially, the slides 14 in table 10 are adjusted particularly in accordance with the desired geometry to be expected due to the particular contour of the pipe. FIG. 2 illustrates symbolically that quite differently dimensioned pipes can readily be accommodated by this test and inspection system.

A pipe R is reeled by means of the roller track of which the first of the set 17 as illustrated in the bottom of FIG. 1 can be regarded as the last set of rollers. The pipe is stopped when the front of the pipe is just over the first pair of transducers 16 of group I. The table 11 is being lifted so that the sensors 20 are properly positioned and the first prism rollers 19 engage the pipe. Now, the pipe is being turned until the seam has straight down or 6 o'clock disposition, symmetrically to the detector 20. The detector 20 continues to monitor the seam position thereafter, and may operate the turning or rotating device for the pipe slightly so that the seam (or better, its center line) remains coincident with axis X.

The table 11 has been lifted and the prism rollers engage the pipe so that the table 11 as a whole, and all the equipment it carries, is positioned in particular relation to the pipe. This way, the entire assembly of test group I is pre-oriented. If the drive 7 continues to apply an upward bias, the rollers 19 (only one at first) are maintained in engagement with the pipe. Any slight irregularities are compensated by the tilt table 11 is permitted to undergo.

Next, the arms 18 carrying the water tanks of the first pair of test heads or transducers are pivoted to test a position in which they engage the pipe. For this, the drives 28 are activated, and are maintained activiated pneumatically. The front end of the tank may be provided with a limit switch which is actuated when engaging the pipe to stop of the drive 28, and, possibly, to switch over to pneumatic operation. Later, after the pipe has passed, the switch disengages which can be used as a signal for causing the drive 28 to retract the arm 18.

Presently, and following the placement of the first pair of test transducers in testing position, the pipe advance is reactuated to, say, half the ultimate test speed while a first test run with that first pair of test heads is carried out.

The pipe is stopped just when the front end reaches the second pair of transducers, and the respective drives 28 are activated to advance the respective water tanks. The pipe is restarted and tests are conducted by both pairs of transducers, whereby the second pair covers the same longitudinal seam portion that was previously covered by the first test pair, but the second test pair is differently oriented to the seam so that the same seam portion is tested as to a different portion and/or as to differently oriented longitudinal flaws, while the first test pair proceeds in its own fashion covering the next longitudinal section of the seam.

The operation proceeds on a stop and go basis as far as the pipe is concerned, and the several transducer pairs are positioned one by one (pair by pair) until the pipe has reached the last test head pair of group I. Having adjusted the position of that test pair, the pipe is now moved at full test speed. As the pipe reaches the first pair of prism rollers 29, the speed is reduced and table 21 is raised by its hydraulic so that the rollers engage and preposition the table 21. As the pipe advances, the arm 27 is swung up so that the tank 22 engages the seam just prior thereto, detector 24 responds to the seam and causes the seam to be centered by turning the pipe if such correction is necessary. It should be noted that the two seam position detectors of unit 20 are farther apart than the two detectors of unit 30, so that the detecting ranges are different. This way, it can be more readily prevented that two control inputs for turning the pipe operable against each other, but an average position of the seam is established.

As tank 22 engages, the four transducers therein begin the inspection as to transverse flaws in the seam. The pipe continues to move and soon reaches the vertical stand 34, the tank 32 is lifted until engaging the pipe, whereupon edge inspection and border zone flaw detection can begin.

Final positioning of table 21 results from pipe engagement with the second set of prism rollers 29. Now, the pipe is accelerated to full speed while all testing units operate. The tail end of the pipe controls sequentially the retraction of all tests heads.

It should be noted that the prism rollers determine the position of the pipe in relation to the tables and the test equipment thereon. The specific disposition of each transducer results from the engagement of the respective water tank with the pipe. These dispositions have been preadjusted as to the test group I by initial adjustment of the carriages or slides 14, and their disposition remains fixed throughout the procedure. The position of the transducer heads results from the pivoting about the arm axes whose positions are fixed through the slides 14, and from actual engagement with the pipe. Therefore, the adjustment remains constant to the extent the pipe's geometry is constant. The cardan mount ensures constant angles of incidence as between transducers and pipes. The automatic follow-up control as to seam position and the stepwise engagement and disengagement of the various transducers and coupler fluid containers permits fully automated operation.

Maintaining the operting parameters constant in this fashion is important if the outputs of the transducers, i.e., the result of the inspection is used in processing equipment for comparison with reference data and reference characteristics as to e.g., echo signal contour and traveling time. Keeping particularly the angles of incidence constant and predetermined, permits meaningful comparison of data to detect even small flaws.

The invention is not limited to the embodiments described above but all changes and modifications thereof not constituting departures from the spirit and scope of the invention are intended to be included.

We claim:

1. Apparatus for inspecting the welding seam and its edge zones of large pipes for purposes of detecting flaws, comprising:

a first table having a plurality of parallelly oriented slide beds, defining directions of sliding transversely to a longitudinal direction along which a pipe to be inspected is moved;

a plurality of slides respectively slidably mounted in the beds;

a plurality of swing arms respectively mounted in the slides for pivoting on axes parallel to said longitudinal direction and extending down from the slides and generally along the lower surface of the pipe, the respective ends of the swing arms are positioned under the pipe for movement in radial direction towards the pipe's surface;

a first plurality of ultrasonic transducers, each said transducer being disposed in a container for coupler fluid, each container having a particular surface for engagement with a pipe thereby to orient the respective transducer in the container relative to the pipe's surface;

means for mounting each of said containers in gimbals and respectively to the ends of the arms to obtain an adjustable disposition of the transducers in the container in relation to the pipe, and for engagement of the respective container with the pipe, whereby the containers engage the pipe in pairs and in symmetric relation to the seam to be inspected;

means for resiliently bias the swing arms in a pivotal direction so that the containers engage the pipe's surface;

means for mutually orienting the table and the seam, so that each transducer in the containers has a particular reproduceable position in relation to the seam as defined by a position adjustment of the respective slide in its bed in the table;

a second plurality of ultrasonic transducers disposed in a container for coupler fluid;

means for mounting said latter container in gimbals;

means for positioning said latter means for mounting so that the transducer of the second plurality are aligned with said table and under the seam and the latter container engages the pipe at the seam;

a pair of transducers disposed in a third container;

means for mounting the third container in gimbals; and means for positioning the means for mounting the third container so that the transducers therein assume testing position in relation to the edge zone of the seam and the third container engages the seam.

2. Apparatus as in claim 1, and including means for mounting said table for positioning for vertical adjustment and tilting about an axis parallel to the pipe's axis.

3. In an apparatus as in claim 1 and including means for driving the swing arms.

4. In an apparatus as in claim 1, the plurality of swing arms including a first and second swing arm the second arm being disposed for symmetric position in relation to the first arm but for independent swing motion.

5. In an apparatus as in claim 1, there being four transducers of the second plurality.

6. In an apparatus as in claim 1 including particular rollers for particularly positioning the pipe, the seam and the axis thereof in fixed relation to said means for mounting.

7. In an apparatus as in claim 6, there being ten such arms, containers and transducers.

* * * * *